United States Patent [19]

Schaffner et al.

[11] 4,288,364

[45] Sep. 8, 1981

[54] FRAGMENTATION PROCEDURE FOR PREPARING 3-AMINO-AZETIDINONES

[75] Inventors: Karl Schaffner, Oberwil; Hansuli Wehrli, Reinach; Beat Müller, Reinach; Riccardo Scartazzini, Basel, all of Switzerland

[73] Assignee: Ciba-Geigy Corporation, Ardsley, N.Y.

[21] Appl. No.: 39,239

[22] Filed: May 15, 1979

[30] Foreign Application Priority Data

May 18, 1978 [CH] Switzerland ..................... 5393/78

[51] Int. Cl.$^3$ .................. C07D 205/08; C07D 120/00; C07D 403/06
[52] U.S. Cl. ........................... 260/239 A; 260/465 D; 260/245.4; 260/330.3; 260/347.3; 260/347.4; 542/413; 542/442; 542/446; 542/455; 560/29; 568/426
[58] Field of Search .............. 260/239 A, 464, 465 D, 260/330.3, 347.3, 347.4, 245.4; 562/448; 544/413, 442, 446, 455

[56] References Cited

PUBLICATIONS

Kunugita et al. Chem. Abs. 86, 153976y (1977).
Moroder et al., Chem. Abs. 86, 107005h (1976).

*Primary Examiner*—Mark L. Berch
*Attorney, Agent, or Firm*—Prabodh I. Almaula

[57] ABSTRACT

When 3-(2-hydroxyiminoacetylamino)-2-oxo-azetidine compounds are treated with reactive derivatives of carbonic acid half-esters in aqueous media in the presence of bases a fragmentation takes place which, in addition to 3-amino-2-oxo-azetidines, also yields nitriles which, compared with the 2-hydroxyiminoacetyl group, have one less carbon atom. The resulting products are intermediates for the preparation of nocardicin-like antibiotics.

The deacylation procedure of this specification offers advantages over the multi-stage deacylation procedure known hitherto, inasmuch as higher yields of 3-amino-2-oxoazetidine compounds are obtained and the acyl group can be obtained in the form of a nitrile which is shorter by one carbon atom.

14 Claims, No Drawings

FRAGMENTATION PROCEDURE FOR PREPARING 3-AMINO-AZETIDINONES

The invention relates to a basic method for the preparation of primary amines and/or nitriles, if desired in a protected form, by splitting the amide bond of 2-hydroxyiminoacetamides by means of a novel fragmentation reaction. The novel amines and nitriles which can be prepared according to the invention, which if desired are in a protected form, are likewise a subject of the invention.

The invention is particularly important for the preparation of 3-amino-2-oxoazetidine compounds, which are valuable starting materials for the preparation of corresponding 3-acylamino-2-oxo-1-azetidine-alkanoic acid derivatives having an antibiotic action. 3-Amino- and 3-acylamino-2-oxo-1-azetidine-alkanoic acid derivatives of this type and processes for their preparation are known, for example, from German Offenlegungsschriften No. 2,529,941 and 2,714,628 and Belgian Patent No. 849,445.

It is known from German Offenlegungsschrift No. 2,529,941 that the 2-hydroxyiminoacetamide compound nocardicin-A (which according to Chemical Abstracts is to be designated (3S)-3-[[[4-((3R)-3-amino-3-carboxypropoxy)phenyl](Z-hydroxyimino)-acetyl]amino]-(αR)-α-(4-hydroxyphenyl)-2-oxo-1-azetidine-acetic acid) can be deacylated in a multi-stage process to the corresponding primary amine, i.e. (3S)-3-amino-(αR)-α-(4-hydroxyphenyl)-2-oxo-1-azetidine-acetic acid (3-amino-lactacillanic acid). This deacylation process is based on the reduction of the 2-hydroxyimino group to the 2-amino group, conversion of the latter to a phenyl- or naphthyl-thioureido group and subsequent detaching of the 2-thioureidoacetyl group by alkaline or acid solvolysis. Alternatively, the 2-amino group can be converted to a 2-nitro-4-methoxyanilino group, after which the corresponding 2-anilinoacetyl group is detached by catalytic hydrogenation under pressure in the presence of aqueous methanol. In both processes the yields are relatively low and, moreover, in each case only the primary amine, i.e. the 3-amino-lactacillanic acid, is isolated. The equally valuable side chain, i.e. 4-(3-amino-3-carboxypropoxy)-phenyl-acetic acid, or any derivative thereof are lost.

The object on which the present invention is based is to detach the 2-hydroxyiminoacetyl group from 3-(2-hydroxyimino-acetyl)-amino-2-oxoazetidine compounds, to prepare the 3-amino-2-oxoazetidine compounds in high yield and purity with the retention of any optically active carbon atoms which may be present and, if desired, also to isolate the 2-hydroxyiminoacetyl side chain in the form of a corresponding nitrile with one less carbon atom.

This object is achieved in a manner superior to the known processes by the surprising fragmentation procedure according to the invention. The superiority of the procedure according to the invention lies in the higher yield, in the possibility for isolation of the said nitriles and in that the procedure can also be carried out as a so-called one-pot process.

The invention accordingly relates to a basic method for the preparation of 3-amino-2-oxoazetidine compounds of the formula

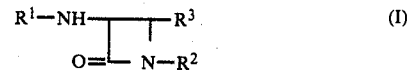

in which $R^1$ is hydrogen or an etherified hydroxycarbonyl group of the formula $R_a{}^1$—O—C(=O)—, in which $R_a{}^1$ is a substituted or unsubstituted hydrocarbon radical, $R^2$ is hydrogen or a substituted or unsubstituted hydrocarbon radical and $R^3$ is hydrogen or a substituted or unsubstituted hydrocarbon radical and functional groups are protected if desired, or salts of such compounds containing salt-forming groups, and/or of nitriles of the formula $R°$—CN, in which $R°$ is a substituted or unsubstituted phenyl or heterocyclyl radical, or salts of such compounds containing a salt-forming group, which comprises treating a 3-(2-hydroxyiminoacetylamino)-2-oxoazetidine compound of the formula

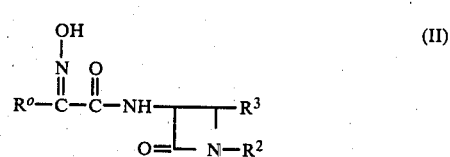

in which $R°$, $R^2$ and $R^3$ are as defined above, in which radicals functional groups are protected if desired, or a salt of such a compound containing a salt-forming group, in an aqueous medium in the presence of a base, with a reactive derivative of a carbon acid half-ester of the formula $R_a{}^1$—O—C(=O)—OH, in which $R_a{}^1$ is as defined above, isolating a compound of the formula I and/or a nitrile $R°$—CN and, if desired, in a resulting compound liberating any protected functional groups which may be present, by detaching the protective groups, or protecting any free functional groups which may be present, and, if desired, converting a resulting compound containing a salt-forming group to a salt or converting a resulting salt to a free compound.

In this Application the term "lower" used to qualify organic radicals, such as lower alkyl, lower alkoxy, lower alkanoyl, lower alkenyl and the like, denotes that these contain not more than 7 and preferably not more than 4 carbon atoms.

Protected functional groups are functional groups protected in a conventional manner, especially protected amino, hydroxyl, mercapto, carboxyl and sulfo groups. Corresponding protective groups are known from peptide, penicillin, cephalosporin and nocardicin chemistry.

In a compound of the formula I and in the reactive derivative of the carbonic acid half-ester of the formula $R_a{}^1$—O—C(=O)—, $R_a{}^1$ is a substituted or unsubstituted aliphatic, cycloaliphatic, aromatic or araliphatic hydrocarbon radical which, for example, contains not more than 18 C atoms and carries, as substituents, for example oxo, lower alkyl, lower alkoxy, halogen, cyano or nitro. Typical radicals $R_a{}^1$ are lower alkyl, such as methyl, ethyl and especially tert.-butyl, oxo-lower alkyl, such as acetonyl, halogeno-lower alkyl, such as 2-bromo- or 2-iodo-ethyl or especially 2,2,2-trichloroethyl, cyano-lower alkyl, such as 2-cyanoethyl, cycloalkyl, such as cyclohexyl, phenyl, which is unsubstituted or substituted by halogen, lower alkoxy or nitro, such as phenyl, pentachlorophenyl, 4-methoxyphenyl or 2-nitrophenyl, and benzyl or diphenylmethyl which can be substituted in the aromatic radical by halogen, lower alkoxy or nitro, such as benzyl, 4-methoxybenzyl, 4-nitrobenzyl, diphenylmethyl or 4,4'-dimethoxydiphenylmethyl.

The substituted or unsubstituted hydrocarbon radical $R^2$ mentioned in the end products of the formula I and the starting materials of the formula II has not more than 18, preferably not more than 12 and in particular 8 carbon atoms. Preferred radicals are the radicals $R^2$ mentioned in the said German Offenlegungsschriften and the Belgian Patent.

Thus, $R^2$ is, for example, a group $-CH(R_a{}^2)(R_b{}^2)$ or a group $-C(R_c{}^2)=C(R_d{}^2)(R_e{}^2)$, in which formulae $R_a{}^2$ is free, esterified or amidated carboxyl or carboxy-lower alkyl, or carboxyl or carboxy-lower alkyl in the form of a salt, cyano, substituted or unsubstituted amino or substituted or unsubstituted hydroxyl, $R_b{}^2$ is lower alkyl, lower alkenyl, cycloalkyl, aryl, heterocyclyl, aralkyl or arylthioalkyl, which radicals are unsubstituted or substituted, for example by lower alkyl, substituted or unsubstituted hydroxyl, substituted or unsubstituted amino, nitro or halogen, $R_c{}^2$ is free, esterified or amidated carboxyl, or carboxyl in the form of a salt, $R_d{}^2$ is hydrogen or lower alkyl and $R_e{}^2$ is lower alkyl or aryl, heterocyclylthioalkyl or arylthio which are unsubstituted or substituted, for example by lower alkyl, substituted or unsubstituted hydroxyl, substituted or unsubstituted amino, nitro or halogen.

In the radicals $R^2$ esterified carboxyl, including in esterified carboxy-lower alkyl, is, for example, esterified by an aliphatic, araliphatic, cycloaliphatic or aromatic alcohol having not more than 18 C atoms and is, for example, lower alkoxycarbonyl, such as methoxy-, ethoxy- or tert.-butoxy-carbonyl, acyloxymethoxycarbonyl, such as pivaloyloxymethoxycarbonyl, halogeno-lower alkoxycarbonyl, such as 2-chloro- or 2,2,2-trichloroethoxycarbonyl, substituted or unsubstituted aryl-lower alkoxycarbonyl, such as benzyloxycarbonyl, 4-methoxy- or 4-nitrobenzyloxycarbonyl, diphenylmethoxycarbonyl or 4,4'-dimethoxydiphenylmethoxycarbonyl, cycloalkyloxycarbonyl, such as cyclohexyloxycarbonyl, substituted or unsubstituted phenoxycarbonyl, such as phenoxycarbonyl or 2- or 4-nitrophenoxycarbonyl, 4-methoxyphenyl, halogenophenoxycarbonyl, such as pentachlorophenoxycarbonyl, and the like.

In the radicals $R^2$ amidated carboxyl, including in amidated carboxy-lower alkyl, is amidated by a primary or secondary aliphatic or aromatic amine or hydrazine or by triazine and is, for example, aminocarbonyl, mono- or di-lower alkylaminocarbonyl, such as methyl- or dimethylaminocarbonyl, anilinocarbonyl, hydrazinocarbonyl or azidocarbonyl.

Substituted or unsubstituted amino in the radicals $R^2$ is, for example, amino, mono- or di-lower alkylamino, acylamino, such as acetylamino, or protected amino, and substituted or unsubstituted hydroxyl is, for example, hydroxyl, lower alkoxy, acyloxy, such as acetoxy or carbamoyloxy, or protected hydroxyl. Protected amino and protected hydroxyl are amino or hydroxyl protected by conventional protective groups, for example by a group $R_1{}^a-O-C(=O)-$ or by another easily detachable acyl group, such as formyl, 2-halogenoacetyl, for example 2-bromo- or 2,2,2-trichloro-acetyl, or by a substituted or unsubstituted benzyl group, such as benzyl, 4-methoxybenzyl or 2- or 4-nitrobenzyl, diphenylmethyl and the like. Protected amino is also phthalimido.

Carboxyl which is in the form of a salt in the radicals $R^2$ is carboxyl which forms one of the metal salts or ammonium salts mentioned below.

In the radicals $R^2$ aryl is an aromatic hydrocarbon, such as phenyl or naphthyl, and heterocyclyl is a 3-membered to 10-membered monocyclic or bicyclic heterocyclyl radical which has one or more heteroatoms from the group comprising nitrogen, oxygen and sulfur and is bonded by one of its C atoms and is, for example, aziridinyl, azetidinyl, pyrrolyl, 2H-pyrrolyl, imidazolyl, pyrazolyl, pyridyl, pyrazinyl, piperidinyl, piperazinyl, pyrimidinyl, pyridazinyl, triazolyl, thiazolinyl, triazinyl, pyrrolidinyl, imidazolidinyl, oxiranyl, furanyl, pyranyl, thienyl, morpholinyl, furazanyl, oxazolyl, isoxazolyl, thiazolyl, thiadiazolyl, oxadiazolyl, indolyl, 3H-indolyl, isoindolyl, indolizinyl, 1H-indazolyl, purinyl, benzimidazolyl, benzotriazolyl, quinolinyl, isoquinolinyl, naphthiridinyl, quinoxalinyl, quinazolinyl, benzofuranyl, chromenyl, isobenzofuranyl, benzothiophenyl, xanthenyl, benzoxazolyl, benzisoxazolyl or benzothiazolyl, which radicals can be substituted as indicated.

$R^2$ is, for example, 1-carboxy-lower alkyl, in which lower alkyl contains one to four C atoms, 1-carboxy-1-arylmethyl, in which aryl is naphthyl or phenyl and in which the phenyl ring is unsubstituted or monosubstituted to trisubstituted by lower alkyl, such as methyl, halogen, such as chlorine or bromine, nitro, substituted or unsubstituted amino and/or substituted or unsubstituted hydroxyl, 1-carboxy-lower alkenyl, 1-carboxy-ω-phenyl-lower alkyl, in which lower alkyl contains two to four C atoms and phenyl can be substituted, for example by hydroxyl, 1-carboxy-ω-heterocyclyl-lower alkyl, in which lower alkyl contains one to four C atoms and heterocyclyl is, for example, thienyl, furyl, thiadiazolyl substituted by lower alkyl, or benzthiazolyl, 1-amino-lower alkyl, in which lower alkyl contains one to four C atoms and amino can be substituted, for example protected, 1-hydroxy-lower alkyl, in which lower alkyl contains one to four C atoms and hydroxyl can be substituted, 1-carboxy-lower alkenyl, in which lower alkenyl contains two to four C atoms and can be substituted by phenyl or phenylthio, in which groups the carboxyl group can be in the esterified or amidated form, for example in the form of lower alkoxycarbonyl, benzyloxycarbonyl, diphenylmethoxycarbonyl and the like or in the form of azidocarbonyl.

Preferred radicals $R^2$ are hydrogen, α-carboxy-4-hydroxybenzyl or α-carboxy-4-hydroxybenzyl, in which the carboxyl group is esterified and/or the 4-hydroxyl group is protected or otherwise substituted, such as α-carbomethoxy-4-methoxybenzyl, α-carbomethoxy-4-benzyloxybenzyl, α-carbobenzyloxy-4-benzyloxybenzyl, α-pivaloyloxymethoxycarbonyl-4-hydroxybenzyl, α-carbomethoxy-4-acetoxybenzyl, α-carboxy-4-benzyloxycarbonyloxybenzyl, α-carboxy-4-tert.-butyloxycarbonyloxybenzyl, α-carboxy-4-benzoyloxybenzyl, α-carboxy-4-(2,2,2-trichloroacetylaminocarbonyloxy)-benzyl, α-diphenylmethoxycarbonyl-4-hydroxybenzyl, α-diphenylmethoxycarbonyl-4-tert.-butoxybenzyl, α-diphenylmethoxy-4-benzyloxycarbonyloxybenzyl, α-carboxybenzyl, α-carbomethoxybenzyl, α-carbobenzyloxybenzyl, α-carbomethoxy-3-amino-benzyl, α-carbomethoxy-3-benzyloxycarbonylaminobenzyl, α-carbomethoxy-3-nitrobenzyl, α-carbomethoxy-4-methylbenzyl, α-carbomethoxy-3,4,5-trimethoxybenzyl, α-carbomethoxy-4-methylthio-benzyl, α-carbomethoxy-3-bromo-4- hydroxybenzyl, α-carboxy-3,5-dibromo-4-hydroxybenzyl, α-carbomethoxy-3,5-dichloro-4-hydroxybenzyl or α-carboxy-4-carbamoyloxybenzyl and also carboxymethyl, carboethoxymethyl, carbobenzyloxymethyl, 1-carboxy-2-methylpropyl, 1-carbomethoxy-2-methylprop-1-en-1-yl, 1-carboethoxy-2-phenylvinyl, 1-carboxy-2-phenylvinyl, 1-carboxy-2-phenylthiovinyl, 1-phenyl-2-carboxyethyl, 1-carboxy-2-phenylthioethyl, 1-carboxy-2-methoxy-2-phenylethyl, 1-carboxy-2-(4-hydroxyphenyl)-ethyl, 1-azidocarbonyl-2-methylpropyl, 1-(2,2,2-trichloroethoxycarbonyl-amino)-2-methylpropyl, 1-tert.-butoxycarbonylamino-2-methylpropyl, 1-acetoxy-2-methyl-propyl, 1-methoxyallyl, carboxy-2-thienylmethyl, carboxy-2-furylmethyl, carboxy-1-naphthyl-methyl, 1-carboxy-3-(5-methyl-1,3,4-thiadiazol-2-yl)-propyl and 1-carboxy-2-methyl-3-benzthiazol-2-yl-propyl.

The substituted or unsubstituted hydrocarbon radicals $R^3$ have not more than 18, preferably not more than 12 and in particular not more than 8 carbon atoms. Preferred radicals are the radicals $R^3$ mentioned in Belgian Pat. No. 849,445, that is to say hydrogen, hydroxymethyl, aryl, especially substituted or unsubstituted phenyl, or aralkenyl, especially substituted or unsubstituted 2-phenylvinyl.

In the starting material of the formula II and in the nitrile of the formula $R°—CN$, $R°$ is, for example, phenyl which is substituted by hydroxyl, etherified or esterified hydroxyl and/or halogen or heterocyclyl which is substituted by hydroxyl, etherified or esterified hydroxyl, halogen and/or substituted or unsubstituted amino.

$R°$ is, for example, hydroxyphenyl, such as 4-hydroxyphenyl, lower alkoxyphenyl, such as 4-methoxyphenyl, lower alkenyloxyphenyl, such as 4-allyloxyphenyl, aralkyloxyphenyl, such as 4-benzyloxyphenyl, lower alkoxycarbonyl-lower alkoxyphenyl, such as 4-methoxycarbonylmethoxyphenyl, carboxy-lower alkoxyphenyl, such as 4-carboxymethoxyphenyl, protected hydroxyphenyl, such as substituted or unsubstituted lower alkoxycarbonyloxyphenyl, for example 4-tert.-butoxycarbonyloxyphenyl, 4-(2,2,2-trichloroethoxycarbonyloxy)-phenyl or 4-benzyloxycarbonyloxyphenyl, ω-carboxy-ω-hydroxy-lower alkoxyphenyl, such as 4-(3-carboxy-3-hydroxypropoxy)-phenyl, ω-carboxy- or ω-lower alkoxycarbonyl-lower alkoxyphenyl, such as 4-(3-carboxypropoxy)-phenyl or 4-(3-methoxycarbonylpropoxy)phenyl, ω-amino-lower alkoxyphenyl in which amino can be protected, such as 4-(3-aminopropoxy)-phenyl, or 4-(3-tert.-butoxycarbonylaminopropoxy)-phenyl, or ω-carboxy-ω-amino-lower alkoxyphenyl in which the carboxyl group and the amino group can be substituted, such as in a protected form. $R°$ is especially 4-(3-carboxy-3-aminopropoxy)phenyl in which carboxyl can be in an esterified form, for example in the form of lower alkoxycarbonyl, such as methoxycarbonyl, in the form of a physiologically splittable ester group, such as lower alkanoyloxymethoxycarbonyl, such as pivaloyloxymethoxycarbonyl, or in the form of an easily splittable ester group, such as in the form of 2,2,2-trichloroethoxy-, benzyloxy-, 4-methoxybenzyloxy-, 2- or 4-nitrophenyloxy- or diphenylmethoxy-carbonyl, and amino can be in an acylated form, for example in the form of substituted or unsubstituted lower alkanoylamino, such as acetylamino, 2-chloroacetylamino, 2,2,2-trifluoroacetylamino, 2-(4-chloro-2-nitrophenoxy)-acetylamino or 2-phenyl-2-sulfoacetylamino, glycylamino, N-phthaloylglycylamino, 2-phenylglycylamino, phthalimido, benzoylamino, substituted or unsubstituted lower alkoxycarbonylamino or lower alkoxythiocarbonylamino, such as tert.-butoxycarbonylamino, 2-chloroethoxycarbonylamino, 2,2,2-trichloroethoxycarbonylamino, 4-methoxybenzyloxycarbonylamino, diphenylmethoxycarbonylamino or ethoxythiocarbonylamino, in the form of substituted or unsubstituted ureido or thioureido, such as 3-phenylureido or 3-phenylthioureido, or in the form of substituted or unsubstituted lower alkyl- or lower alkenyl-amino, such as dimethylamino, isopropylamino, 2-carbomethoxyethylamino, 2-carboxyethylamino, sulfomethylamino, 1-sulfoethylamino, tritylamino or 2-carbomethoxy-1-methylvinylamino, or in the form of substituted arylamino, such as 2-nitro-4-carbomethoxyanilino, and in which the phenyl group is unsubstituted or substituted by halogen, such as chlorine. $R°$ is, furthermore, one of the substituted or unsubstituted heterocyclic radicals mentioned under $R^2$, such as furyl, for example 2-furyl, thienyl, for example 2-thienyl, or thiazolyl, for example 2-amino- or 2-(2,2,2-trifluoroacetamido)-1,3-thiazol-4-yl.

Starting compounds of the formula II can be employed in the racemic or optically active form and the hydroxyimino group can be in the Z-position or E-position. Preferably, the starting compounds of the formula II which are employed are those in which the asymmetrically substituted C atoms which are present have the conformations corresponding to the corresponding C atoms of nocardicin A.

The invention is of particular importance for the deacylation of compounds of the formula II which can be prepared by fermentation. Accordingly, compounds of the formula II which can be prepared by fermentation are preferred as starting materials (cf. British Patent Specification No. 1,388,198 and German Offenlegungsschrift No. 2,242,699 which corresponds thereto), especially nocardicin A, which has already been mentioned, and also nocardicin B (the E-isomer to nocardicin A), nocardicin E (which according to Chemical Abstracts is to be designated as (3S)-3-[[(Z-hydroxyimino)(4-hydroxyphenyl)-acetyl]amino](αR)-α-(4-hydroxyphenyl)-2-oxo-1-azetidine-acetic acid) and nocardicin F (E-isomer of nocardicin E).

In the starting material of the formula II, functional groups, except for the hydroxyimino group, can be in the free or protected form. In the course of the procedure, acylatable groups, such as hydroxyl and amino groups, are acylated by the reactive derivative of the carbonic acid half-ester of the formula $R_a{}^1—O—C(=O)—OH$. After the reaction has ended, acylatable groups present in the products of the formula I and in the nitrile $R^0—CN$ are therefore initially in the form acylated by the group $R_a{}^1—O—C(=O)—$. Depending on the manner of working up, the acyl groups $R_a{}^1—O—C(=O)—$ or other protective groups present can be detached.

Salts of compounds of the formulae I, II or $R^0—CN$ are, in particular, salts of those compounds which contain an acid grouping, such as a carboxyl or sulfo group, and in particular metal salts or ammonium salts, such as alkali metal salts and alkaline earth metal salts, for example sodium, potassium, magnesium or calcium salts, and also ammonium salts with ammonia or suitable organic amines, suitable compounds for forming the salts being, in particular, aliphatic, cycloaliphatic, cycloaliphaticaliphatic and araliphatic primary, secondary or tertiary mono-, di- or poly-amines, and also heterocyclic bases, such as lower alkylamines, for example triethylamine, hydroxy-lower alkylamines, for example 2-hydroxyethylamine, di-(2-hydroxyethyl)-amine or tri-(2-hydroxyethyl)-amine, basic aliphatic esters of carboxylic acids, for example 2-diethylaminoethyl 4-aminobenzoate, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae I, II or $R^0$—CN which contain a basic group can form acid addition salts, for example with inorganic acids, such as hydrochloric acid, sulfuric acid or phosphoric acid, or with suitable organic carboxylic or sulfonic acids, for example trifluoroacetic acid or p-toluenesulfonic acid. Compounds of the formulae I, II or $R^0$—CN which contain an acid group and a basic group can also be in the form of inner salts, i.e. in zwitterionic form.

The reactive functional derivatives of a carbonic acid half-ester of the formula $R_a^1$—O—C(=O)—OH which are to be used for carrying out the procedure are in particular anhydrides, mixed anhydrides, especially with hydrogen halide acids or hydrazoic acid, and reactive esters, such as with halogenophenols, for example with 2,4,5-trichlorophenol, or with hydroxyimino compounds, for example with 2-hydroxyimino-2-phenylacetonitrile. Such compounds are known from peptide, penicillin, cephalosporin and nocardicin chemistry as reagents for protecting amino and hydroxyl groups. Preferred compounds are corresponding halogenoformic acid esters, such as chloroformic acid esters, for example 2,2,2-trichloroethoxycarbonyl chloride, tert.-butoxycarbonyl chloride, carbobenzoxy chloride, 4-methoxycarbobenzoxy chloride and 4-nitrocarbobenzoxy chloride, or fluoroformic acid esters, for example tert.-butoxycarbonyl fluoride, or azidoformic acid esters, for example tert.-butoxycarbonyl azide, reactive 2,4,5-trichlorophenyl esters, for example tert.-butyl-2,4,5-trichlorophenyl carbonate and 4-methoxybenzyl-2,4,5-trichlorophenyl carbonate, or reactive hydroxyimino esters, for example 2-tert.-butoxycarbonyloxyimino-2-phenylacetonitrile, and especially symmetrical anhydrides, for example di-tert.-butyl dicarbonate.

Suitable aqueous media, in which the procedure is carried out, are any water-miscible, non-nucleophilic, organic solvents, for example ethers, such as tetrahydrofuran, or polyethers, such as etherified ethylene glycols or polyethylene glycols, for example diethoxyethane, or cyclic polyethylene oxides, for example dioxan, or Crown ethers, such as 15-Crown-5 or 18-Crown-6, ketones, such as alkyl ketones, for example acetone, amides, such as di-lower alkylamides, for example dimethylformamide, lower alkylated phosphoric acid triamide, such as hexametapol, or di-lower alkylsulfoxides, such as dimethylsulfoxide, which contain at least one equivalent and in general up to about 500 equivalents (based on the starting material employed) of water.

Suitable bases are the inorganic or organic bases customary in acylation reactions, for example alkali metal bases or alkaline earth metal bases, such as hydroxides or carbonates of sodium, potassium or calcium, especially sodium hydroxide and sodium carbonate, and also organic tertiary nitrogen bases, such as tri-lower alkylamines, for example triethylamine or ethyl diisopropylamine, N,N-di-lower alkylanilines, such as N,N-dimethylaniline, or cyclic nitrogen bases, such as 1,5-diazabicyclo[5.4.0]undec-5-ene or 1,5-diazabicyclo[4.3.0]non-5-ene.

The reactive functional derivative of a carbonic acid half-ester of the formula $R_a^1$—O—C(=O)—OH is added at a temperature from room temperature up to about 100° C. If, in addition to the hydroxyimino group, yet further acylatable functional groups, such as amino or hydroxyl groups, are present in the starting material of the formula II, these are acylated by the acylating reagent used, either preferentially or at the same time as the hydroxyimino group to be acylated. For example, an amino group can be acylated preferentially at room temperature. The acylation of the hydroxyimino group can likewise be carried out at low temperature, whilst the subsequent fragmentation is advantageously carried out at elevated temperature, i.e. at 40°-80° and preferably at 50°-60°.

The amount of the acylating agent to be used depends on the number of acylatable functional groups in the starting material and on whether the amine of the formula I in which $R^1$ is hydrogen, which first forms during the fragmentation, is to be completely converted to an acylated amine of the formula I in which $R^1$ is a group $R_a^1$—O—C(=O)— and on whether any hydroxyl groups which may be present, especially phenolic hydroxyl groups, are likewise to be completely acylated. Preferably, the acylating agent is added in an amount such that, at the end of the reaction, all of the acylatable groups in the end products have been acylated by the group $R_a^1$—O—C(=O)—. Since the reactive functional derivative of the carbonic acid half-ester which is to be used is partly hydrolysed in the aqueous medium in the course of the reaction, an excess of this derivative must be used and this is added up to the end of the reaction, if necessary at low temperatures. It is also possible first to carry out fragmentation with an acylating agent, for example carbobenzoxy chloride, and then to acylate any phenolic hydroxyl groups which may still be present with a second acylating agent, for example di-tert.-butyl dicarbonate.

The progress of the reaction can be followed by UV spectrophotometry or by thin layer chromatography.

The resulting compound of the formula I can be separated from the nitrile of the formula $R^0$—CN, which forms at the same time, by conventional methods of separation, such as crystallisation, chromatography or partitioning operations; alternatively, a mixture which is first obtained is converted to derivatives (for example resulting compounds containing carboxyl groups can be converted to esters, such as diphenylmethyl esters) and the resulting derivatives are then separated.

In a resulting compound of the formula I, in a resulting nitrile $R^0$—CN or in a resulting mixture thereof, any free functional groups which may be present and which are not acylatable under the fragmentation conditions, especially free acid groups, for example free carboxyl groups, can be protected in a manner known per se, especially by esterification; the resulting esters should be easily splittable again. Numerous esters of this type are known and include, in particular, lower alkyl esters, such as methyl, ethyl or tert.-butyl esters, halogenolower alkyl esters, such as 2,2,2-trichloroethyl or 2-iodoethyl esters, 2-keto-lower alkyl esters, such as acetonyl esters or phenacyl esters, 2-cyano-lower alkyl esters, such as 2-cyanoethyl esters, benzyl esters, which can be substituted on the $CH_2$ group by lower alkyl or phenyl and/or in the phenyl ring by nitro, lower alkoxy or halogen, such as benzyl, 2- or 4-nitrobenzyl, 2-methoxybenzyl, 3,4-dimethoxybenzyl or 4-chlorobenzyl esters, diphenylmethyl or 4,4'-dimethoxydiphenylmethyl esters, or trityl esters, or phenyl esters which can be substituted by nitro or halogen, such as 2- or 4-nitrophenyl or pentachlorophenyl esters.

The esterification is carried out by the conventional methods, for example by treatment with a corresponding conventional esterifying agent, such as a halide compound, for example methyl iodide, ethyl iodide, benzyl chloride, phenacyl bromide and the like; a corresponding sulfate, such as dimethyl sulfate, diethyl sulfate and the like, a corresponding sulfonate, such as methyl benzenesulfonate or ethyl benzenesulfonate, or methyl p-toluenesulfonate or ethyl p-toluenesulfonate, or methyl fluorosulfonate or methyl trifluoromethylsulfonate and the like; a corresponding diazo compound, such as diazomethane, diphenyldiazomethane and the like; or a corresponding alcohol, such as methanol, 2,2,2-trichloroethanol and the like, if necessary in the presence of a condensing agent.

In the case of esterification with a halide, sulfate or sulfonate, the reaction is carried out in the presence of a base, such as one of the bases mentioned for the main reaction, or the acid compound is employed in the form of a salt, for example in the form of an alkali metal salt. If an alcohol is used as the esterifying agent, conventional condensing agents, such as a carbodiimide, for example N,N'-dicyclohexylcarbodiimide, N-cyclohexyl-N'-morpholinoethylcarbodiimide or N,N'-diethylcarbodiimide, are used. The esterification is carried out in one of the conventional solvents, at room temperature or at lowered or elevated temperature.

In a resulting compound of the formula I or in a resulting nitrile $R^0$—CN with protected functional groups, the protective groups can be detached in a conventional manner. If several protected functional groups are present, the protective groups can be detached at the same time, selectively or successively, depending on the nature of the protective group and on the nature of the detaching reaction.

For example, a tert.-butoxycarbonylamino or diphenylmethoxycarbonylamino group can be split by treatment with formic acid, trifluoroacetic acid or p-toluenesulfonic acid, a 2,2,2-trichloroethoxycarbonylamino or 2-iodoethoxycarbonylamino group or a p-nitrobenzyloxycarbonylamino group can be split by treatment with suitable reducing agents, such as zinc in the presence of aqueous acetic acid or hydrogen in the presence of a palladium catalyst, a tert.-butoxycarbonyloxy group can be split by treatment with formic acid or trifluoroacetic acid, or a 2,2,2-trichloroethoxycarbonyloxy group or p-nitrobenzyloxycarbonyloxy group can be split by treatment with a chemical reducing agent, such as zinc in the presence of aqueous acetic acid, or with hydrogen in the presence of a palladium catalyst, splitting being carried out selectively if desired.

A carboxyl group esterified by a suitable 2-halogeno-lower alkyl group, an arylcarbonylmethyl group or a 4-nitrobenzyl group can be converted to a free carboxyl group, for example by treatment with a chemical reducing agent, such as a metal, for example zinc, or a reducing metal salt, such as a chromium-II salt, for example chromium-II chloride, usually in the presence of a hydrogen donor which, together with the metal, is able to produce nascent hydrogen, such as an acid, in particular acetic acid and also formic acid, or of an alcohol, in which case water is preferably added, a carboxyl group esterified by an arylcarbonylmethyl group can also be converted to a free carboxyl group by treatment with a nucleophilic, preferably salt-forming reagent, such as sodium thiophenolate or sodium iodide, and a carboxyl group esterified by 4-nitrobenzyl can also be converted to a free carboxyl group by treatment with an alkali metal dithionite, for example sodium dithionite. A carboxyl group esterified by a suitable arylmethyl grouping can be split and set free, for example, by irradiation, preferably with ultraviolet light, for example under 290 m$\mu$, if the arylmethyl group is, for example, a benzyl radical which is unsubstituted or substituted in the 3-, 4- and/or 5-position, for example by lower alkoxy and/or nitro groups, or with longer wave ultraviolet light, for example above 290 m$\mu$, if the arylmethyl group is, for example, a benzyl radical substituted in the 2-position by a nitro group, and, furthermore, a carboxyl group esterified by a suitably substituted methyl group, such as tert.-butyl or diphenylmethyl, can be split and set free, for example, by treatment with a suitable acid agent, such as formic acid or trifluoroacetic acid, if necessary with the addition of a nucleophilic compound, such as phenol or anisole, and a hydrogenolytically splittable esterified carboxyl group, for example benzyloxycarbonyl or 4-nitrobenzyloxycarbonyl, can be split and set free by hydrogenolysis, for example by treatment with hydrogen in the presence of a noble metal catalyst, for example a palladium catalyst. A 2-oxoethoxycarbonyl or 2-cyanoethoxycarbonyl group which is unsubstituted or substituted in the 2-position by lower alkyl or aryl, for example the acetonyloxycarbonyl or 2-cyanoethoxycarbonyl group, can be converted under mild conditions, i.e. at room temperature or with cooling, by treatment with a suitable base to the corresponding salt of this carboxyl group, from which the free carboxyl group is obtainable by acidification. Suitable bases are metal bases, such as alkaline earth metal bases and especially alkali metal bases, which have a nucleophilic reaction, such as corresponding hydroxides, carbonates, bicarbonates, alkoxides, phenolates, mercaptides, thiophenolates or amides, for example sodium hydroxide, sodium carbonate, sodium bicarbonate, sodium ethanolate, sodium thiophenolate, sodium amide or sodium morpholide or corresponding lithium or potassium compounds, which are used in water, aqueous solvents or solvents containing hydroxyl groups or also in polar inert solvents with subsequent treatment with water. Tertiary amines, such as a tri-lower alkylamine, for example triethylamine or Hünig's base, or cyclic or bicyclic amines or imines, such as N-methylmorpholine or 1,5-diazabicyclo[5.4.0]undec-5-ene, in an inert solvent, such as methylene chloride or tetrahydrofuran, can also be used to split the 2cyanoethoxycarbonyl groups and in this case the corresponding ammonium salts of the carboxyl compound are obtained direct. A pentachlorophenyloxycarbonyl group can be converted to a free carboxyl group under mild conditions, for example by dilute sodium carbonate or sodium bicarbonate solution or by an organic base in the presence of water.

The detaching of protective groups can, if desired, be effected selectively or simultaneously.

Thus, a tert.-butoxycarbonylamino group can be converted selectively by treatment with p-toluenesulfonic acid to the free amino group or to the corresponding p-toluenesulfonic acid salt thereof, and tert.-butoxycarbonyloxy groups or diphenylmethoxycarbonyl groups which are present at the same time are not split. On the other hand, a tert.-butoxycarbonyloxy group can be split to the hydroxyl group by treatment with bases, such as aqueous sodium carbonate solution, and tert.-butoxycarbonylamino and diphenylmethoxycarbonyl groups which are present at the same time are not split. The tert.-butoxycarbonylamino group, the tert.-butoxycarbonyloxy group and the diphenylmethoxycarbonyl group can be split at the same time by treatment with trifluoroacetic acid, if appropriate in the presence of anisole.

Salts of compounds of the formula I and of nitriles of the formula $R^0$—CN can be prepared in a manner known per se. Thus, salts of those compounds which contain acid groups can be formed, for example, by treatment with metal compounds, such as alkali metal salts of suitable carboxylic acids, for example the sodium salt of α-ethylcaproic acid, or with ammonia or a suitable organic amine and preferably stoichiometric amounts or only a small excess of the salt-forming agent are used. Acid addition salts of compounds containing basic groupings are obtained in the conventional manner, for example by treatment with an acid or a suitable anion exchange reagent. Inner salts of compounds which contain, for example, a salt-forming amino group and a free carboxyl group can be formed, for example, by neutralising salts, such as acid addition salts, to the isoelectric point, for example with weak bases, or by treatment with liquid ion exchangers.

Salts can be converted to the free compounds in a conventional manner, metal and ammonium salts, for example, can be converted by treatment with suitable acids and acid addition salts can be converted, for example, by treatment with a suitable basic agent.

Resulting mixtures of isomers can be separated into the individual isomers by methods known per se; mixtures of diastereomeric isomers, for example, can be separated by fractional crystallisation, adsorption chromatography (column or thin layer chromatography) or other suitable methods of separation. Resulting racemates can be resolved into the antipodes in a conventional manner, if appropriate after introducing suitable salt-forming groupings, for example by forming a mixture of diastereomeric salts with optically active salt-forming agents, separating the mixture into the diastereomeric salts and converting the salts into the free compounds, or by fractional crystallisation from optically active solvents.

The procedure also includes those embodiments in which compounds obtained as intermediates are used as starting materials and the remaining process steps are carried out with these, or the process is discontinued at any stage; furthermore, starting materials can be used in the form of derivatives or can be formed in situ, in some cases under the reaction conditions.

The invention also relates to the novel compounds of the formula I, especially those in which $R^1$ is an esterified hydroxycarbonyl group of the formula $R_a^1$—O—C(=O)—.

These compounds are valuable intermediates which have the advantage over the known compounds of the formula I in which $R^1$ is hydrogen that they are more stable and therefore can be stored more easily.

Preferred novel compounds of the formula I are those in which $R^1$ is an esterified hydroxycarbonyl group of the formula $R_a^1$—O—C(=O)—, in which $R_a^1$ is as defined and is especially lower alkyl, preferably tert.-butyl, or benzyl which is unsubstituted or substituted in the phenyl ring by halogen, lower alkoxy or nitro, $R^2$ is as defined and is especially an α-carboxy-4-hydroxybenzyl group, in which carboxyl and hydroxyl can be in a protected form, carboxyl for example in the form of an ester, such as the diphenylmethyl ester, and hydroxyl for example in the form of a tert.-butoxycarbonyloxy or benzyloxycarbonyloxy group, and $R^3$ is hydrogen, and which at the asymmetric C atom have the conformation of naturally occuring nocardicins.

The invention likewise relates to the novel compounds of the formula $R^0$—CN, in which $R^0$ is in particular ω-carboxy-ω-amino-lower alkoxyphenyl, in which carboxyl and amino can be in a protected form.

These nitriles are valuable intermediates which can be converted by a conventional route to the 2-$R^0$-2-oxo- and 2-$R^0$-2-hydroxyimino-acetic acids which are known from German Offenlegungsschrift No. 2,714,628 and which, in turn, are valuable acylating agents and starting materials for the synthesis of 3-acylamino-2-azetidinone compounds.

The conversion of the nitriles $R^0$—CN to the 2-oxo- and the 2-hydroxyimino-acetic acids can take place, for example, in accordance with the following reaction equation:

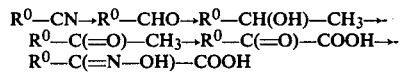

An aldehyde $R^0$—CHO is obtained by treating a nitrile $R^0$—CN, in which functional groups can be in a protected form, with a reducing agent and hydrolysing the intermediate first formed.

Suitable reducing agents are, for example, lithium tri-lower alkoxy-aluminium hydride, such as lithium triethoxy-aluminium hydride, tin-II chloride and catalytically activated hydrogen, for example hydrogen activated with Pd(OH)$_2$/BaSO$_4$ or Raney nickel. The reduction is carried out in an inert solvent, for example an ether or, in the case of catalytic hydrogenation, also in an alcohol, such as methanol, if appropriate in the presence of dianilinoethane, at room temperature or a slightly lowered or elevated temperature. The intermediate first formed is then hydrolysed by means of water or dilute acids to give the aldehyde.

In a resulting aldehyde $R^0$—CHO, the functional groups can be protected, or protected functional groups can be set free. For the subsequent reactions, carboxyl groups which are present are advantageously esterified, for example with a diazo compound, such as diphenyldiazomethane.

The novel aldehydes $R^0$—CHO and the process for their preparation are likewise a subject of the present invention.

A hydroxyethyl compound $R^0$—CH(OH)—CH$_3$ is obtained by treating an aldehyde $R^0$—CHO, in which functional groups can be in a protected form, with a methyl-Grignard compound.

Methyl-Grignard compounds used are the customary methyl-magnesium halides, such as the chloride, bromide or iodide. Carboxyl and amino groups in the aldehyde $R^0$—CHO employed are preferably in a protected form.

The Grignard reaction is carried out in the conventional manner in an inert solvent, for example an ether, such as diethyl ether and/or tetrahydrofuran, at room temperature or a slightly lowered or elevated temperature.

The novel hydroxyethyl compounds R⁰—CH(OH)—CH₃ and the process for their preparation are likewise a subject of the invention.

A ketone R⁰—C(=O)—CH₃ is obtained by oxidising a hydroxyethyl compound R⁰—CH(OH)—CH₃.

The oxidising agents used are the reagents customary for converting secondary alcohols to ketones, such as alkali metal dichromates, for example sodium dichromate or potassium dichromate, chromium trioxide, N-halogenoamides, such as N-bromoacetamide, N-bromosuccinimide or N-chlorosuccinimide, sulfoxides, such as dimethylsulfoxide, and especially manganese dioxide.

The oxidation is carried out in one of the customary solvents, at room temperature or a slightly lowered or elevated temperature. Preferably, the oxidising agents and solvents used are those with which any protective groups present in the starting material are not detached. An oxidising system of this type is, for example, manganese dioxide in methylene chloride.

If desired, protective groups present in a resulting ketone R⁰—C(=O)—CH₃ can be detached by the conventional methods, and/or free functional groups can be protected.

The process for the preparation of the ketones R⁰—C(=O)—CH₃ is likewise a subject of the present invention.

Certain ketones R⁰—C(=O)—CH₃ and alternative processes for their preparation are already known from German Offenlegungsschrift No. 2,714,628. The further processing to the 2-oxoacetic acids R⁰—C(=O)—COOH and the 2-hydroxyiminoacetic acids is also known from the said German Offenlegungsschrift.

In the compounds R⁰—CN, R⁰—CHO and R⁰—CH(OH)—CH₃, R⁰ is preferably a radical which occurs in compounds of the formula II which are obtainable by fermentation and is in particular the 4-((3R)-3-carboxy-3-aminopropoxy)phenyl radical, in which carboxyl and amino can be in a protected form.

The present invention is illustrated in more detail in the following non-limiting examples, in which the following abbreviation is used: TLC=thin layer chromatogram on silica gel. The temperatures are given in degrees centigrade.

EXAMPLE 1

1.5 ml (6.8 mmoles) of di-tert.-butyl dicarbonate are added in the course of 10 minutes, at room temperature, to a solution of 1 g of the sodium salt of nocardicin A [M. Hashimoto, T. Komore and R. Kamiya, J. Amer. Chem. Soc. 98, 3,023 (1976)] in a suspension of 4 g (38 mmols) of sodium carbonate in 24 ml of water and 40 ml of dioxan. The mixture is warmed to 45° and a further 4 ml of di-tert.-butyl dicarbonate are added dropwise in the course of 5 days (about 1 drop per hour), with stirring. After cooling, a further 1 ml of this reagent is added to the mixture and the mixture is stirred for a further 2 hours at room temperature. 100 ml of water are added to the mixture and the latter is extracted with twice 200 ml of methylene chloride. The aqueous phase is cooled to 0°–5° and 170 ml of ice-cold 5 percent citric acid are added (pH of the mixture 4). The mixture is extracted with three times 500 ml of ethyl acetate and the organic phase is washed with twice 100 ml of sodium chloride solution, dried by means of magnesium sulfate and evaporated, yielding 1.4 g of a mixture of 4-((3R)-3-tert.-butoxycarbonylamino-3-carboxypropoxy)-benzonitrile and (3S)-3-tert.-butoxycarbonylamino-(αR)-α-(4-hydroxyphenyl)-2-oxo-1-azetidine-acetic acid. This mixture is dissolved in 10 ml of methanol, and 100 ml of ether and 1.5 g (8.1 mmols) of diphenyldiazomethane are added to the solution. The mixture is stirred overnight at room temperature and on the next day is evaporated in vacuo, yielding 2.8 g of a crude mixture, which is chromatographed on 100 g of silica gel impregnated with 1:1 toluene:methylene chloride. Elution with methylene chloride yields 0.666 g (70.3%) of 4-((3R)-3-diphenylmethoxycarbonyl-3-tert.-butoxycarbonylaminopropoxy)benzonitrile. IR absorption spectrum (in CH₂Cl₂): characteristic bands at 3,400, 2,250, 1,740 and 1,715 cm⁻¹; NMR spectrum (DMSO-d₆):

| δ Values (ppm) | Number of H | Assigned to |
| --- | --- | --- |
| 1.4 s | 9 | tert.-butyl-CH₃ |
| 2.0–2.4 m | 2 | 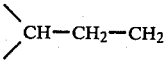 |
| 4.15 t | 2 | O—CH₂—CH₂; J = 6Hz |
| 4.2–4.5 m | 1 | —NH—CH—COOR |
| 7.15 and 7.75 q | 4 | 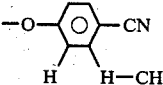 |
| 6.85 s | 1 | |
| 7.2–7.6 m | 10 | phenyl-H + 1 NH |

Further elution with methylene chloride yields 539 mg (46%) of diphenylmethyl (3S)-3-tert.-butoxycarbonylamino-(αR)-α-(4-tert.-butoxycarbonyloxyphenyl)-2-oxo-1-azetidineacetate. IR absorption spectrum (in CH₂Cl₂): characteristic bands at 3,400, 1,760 and 1,720 cm⁻¹; NMR spectrum (DMSO-d₆):

| δ Values (ppm) | Number of H | Assigned to |
| --- | --- | --- |
| 1.38 s | 9 | tert.-butyl-CH₃ |
| 1.49 s | 9 | tert.-butyl-CH₃ |
| 3.1–3.2 m | 1 | 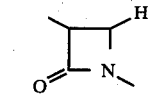 |
| 3.65–3.85 t | 1 | 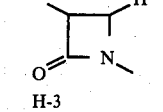 |
| 4.5–4.8 broad | 1 | H-3 |
| 5.82 s | 1 | 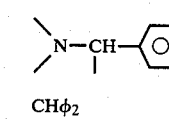 |
| 6.85 s | 1 | CHφ₂ |
| 7.0–7.8 m | 14 | Ar—H + 1 NH |

Further elution with 98:2 methylene chloride:methanol yields 0.422 g (46% of theory) of diphenylmethyl (3S)-3-tert.-butoxycarbonylamino-(αR)-α-(4-hydroxyphenyl)-2-oxo-1-azetidineacetate. IR absorption spectrum (in CH₂Cl₂): characteristic bands at 3,620, 3,530, 1,760, 1,745 and 1,720 cm⁻¹; NMR spectrum (DMSO-d₆):

| δ Values (ppm) | Number of H | Assigned to |
| --- | --- | --- |
| 1.32 s | 9 | tert.-butyl-CH$_3$ |
| 3.0 q | 1 | 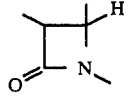 |
| 3.65 t | 1 | |
| 4.65 broad | 1 | H-3 |
| 5.60 s | 1 | N—CH—Ar |
| 6.84 s | 1 | 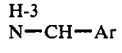 CH$\phi_2$ |
| 7.0–7.7 | 14 | ArH + 1 NH |

EXAMPLE 2

1,200 ml of dioxan and 40 g (0.076 mol) of nocardicin A are added to a solution of 160 g of sodium carbonate in 600 ml of water. The mixture is warmed to 30° and 52 ml (0.238 mol) of di-tert.-butyl dicarbonate are added dropwise in the course of 30 minutes. After adjusting the internal temperature to 55° C., a further 52 ml (0.238 mol) of di-tert.-butyl dicarbonate are added dropwise in the course of 24 hours, after which the absorption at 250 nm reaches a maximum. Before working up, the mixture is cooled to 30° and a further 40 ml (0.183 mol) of di-tert.-butyl dicarbonate are added dropwise in the course of 24 hours, after which only two spots, corresponding to the products, are detectable in the TLC. The mixture is cooled to 15°–20° and the inorganic salts are filtered off with suction. The residue is washed thoroughly with dioxan and the filtrate is evaporated at 10° (solid carbon dioxide cold trap) to about 750 ml. This residue is cooled to 0°–5° and extracted with three times 500 ml of ethyl acetate. The pH of the aqueous phase is adjusted to 4 at 0°–5° using concentrated citric acid and this phase is immediately extracted with three times 600 ml of ethyl acetate. The organic phase is washed with twice 100 ml of sodium chloride solution, dried over magnesium sulfate and evaporated to about 200 ml. The product which had precipitated is filtered off with suction and washed with ethyl acetate until colourless, yielding 25.4 g (75% of theory) of pure (3S)-3-tert.-butoxycarbonylamino-(αR)-α-(4-tert.-butoxycarbonyloxyphenyl)-2-oxo-1-azetidineacetic acid. Melting point 195° (with decomposition); $[\alpha]_D^{20} = -156° \pm 1°$ (0.5 M NaHCO$_3$). IR absorption spectrum (Nujol): characteristic bands at 3,670, 1,755, 1,735 and 1,705 cm$^{-1}$; NMR spectrum (in DMSO-d$_6$):

| δ Values (ppm) | Number of H | Assigned to |
| --- | --- | --- |
| 1.37 s | 9 | t.-butyl-CH$_3$ |
| 1.50 s | 9 | t.-butyl-CH$_3$ |
| 3.10 q | 1 | 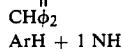 |
| 3.78 t | 1 | |
| 4.71 broad | 1 | |
| 5.50 s | 1 | N—CH—COOH |
| 7.23 and 7.45 q | 4 | aromatic A$^2$B$^2$ |
| 7.60 d | 1 | NH J = 8 Hz |

After adding a little ether, 18.1 g (74% of theory) of 4-((3R)-3-tert.-butoxycarbonylamino-3-carboxypropoxy)benzonitrile with a melting point of 132°–146° crystallise from the mother liquor; this product is recrystallised from ether to give the analytically pure product, a product with a melting point of 144°–145° being obtained. $[\alpha]_D^{20} = -8° \pm 1°$ (0.5 M NaHCO$_3$). IR absorption spectrum (Nujol): characteristic bands at 3,400, 2,270, 1,775 sh, 1,720 and 1,610 cm$^{-1}$; UV spectrum: $\lambda_{max}^{0.5\ M\ NaHCO_3} = 2,500$ nm ($\epsilon = 22,000$).

| NMR Spectrum (in DMSD-d$_6$) | δ Values (ppm) | Number of H | Assigned to |
| --- | --- | --- | --- |
| | 1:38 s | 10 | t.-butyl-CH$_3$ |
| | 1.95–2.35 broad | 2 | CH—CH$_2$—CH$_2$ |
| | 4.14 t | 3 | CH—CH$_2$ + O—CH$_2$—CH$_2$ (J = 6 Hz) |
| | 7.08 and 7.71 q | 4 | aromatic A$^2$B$^2$ (J = 9 Hz) |

EXAMPLE 3

20 g (0.038 mol) of nocardicin A are dissolved in a suspension of 80 g (0.76 mol) of Na$_2$CO$_3$ in 300 ml of water and 600 ml of dioxan, and 26 ml (0.117 mol) of di-tert.-butyl dicarbonate are added in the course of 10 minutes at 30°. The mixture is warmed to 40° and a further 54 ml (0.243 mol) of di-tert.-butyl dicarbonate are added in the course of 9 days (about 4 drops per hour), with stirring. At a bath temperature of 25° 400 ml of water/dioxan mixture are distilled off under a water-pump vacuum. The residue is brought into solution by adding 4 liters of water and the solution is extracted with four times 500 ml of methylene chloride. The organic phase is washed with 1 liter of water and an emulsion forms, but this separates after a few minutes. Ice is added to the aqueous phase and this phase is covered with a layer of 4 liters of ice-cooled ethyl acetate. At 0°–5°, the pH of the mixture is adjusted to 4 with 10 percent citric acid. The aqueous phase is washed twice more with, in each case, 3 liters of ethyl acetate. The organic phase is washed with twice 1 liter of sodium chloride solution, dried over MgSO$_4$ and evaporated at 25° in vacuo, yielding a mixture consisting of 4-((3R)-3-tert.-butoxycarbonylamino-3-carboxypropoxy)-benzonitrile, (3S)-3-tert.-butoxycarbonylamino-(αR)-α-(4-tert.-butoxycarbonyloxyphenyl)-2-oxo-1-azeitidineacetic acid and (3S)-3-tert.-butoxycarbonylamino-(αR)-α-(4-hydroxyphenyl)-2-oxo-1-azetidineacetic acid.

26.3 g of this acid mixture are dissolved in 1 liter of dioxan and 20 g (0.1 mol) of diphenyldiazo methane are added. The dark red solution is stirred overnight at room temperature and according to the TLC all of the starting material is converted. The slightly red coloured mixture is evaporated in vacuo and 47 g of a crude ester mixture are obtained and this is chromatographed on 2 kg of silica gel extra pure (Merck) impregnated with 1:1 toluene:methylene chloride. Elution of the column with methylene chloride yields 11.9 g (65% of crude product) of 4-((3R)-3-diphenylmethoxycarbonyl-3-tert.-butoxycarbonylaminopropoxy)-benzonitrile, from which 9.5 g (52% of theory) of pure product with a melting point of 127°–129°, and an $[\alpha]_D^{20} = -3° \pm 1°$ (1% in chloroform) is obtained by crystallisation from ether. The IR, UV and NMR spectra are identical with those for the product obtained according to Example 1.

Further elution yields 9.5 g (42% of crude product) of diphenylmethyl (3S)-3-tert.-butoxycarbonylamino-(αR)-α-(4-tert.-butoxycarbonyloxyphenyl)-2-oxo-1-azetidineacetate, from which 3.8 g (17% of theory) of pure product with a melting point of 155°–157° are obtained by crystallisation from ether followed by crystallisation from absolute ethanol; the pure product is identical to the product from Example 1.

Further elution with 98:2 methylene chloride: methanol yields 7.7 g (40% of crude product) of diphenylmethyl (3S)-3-tert.-butoxycarbonylamino-(αR)-α-(4-hydroxyphenyl)-2-oxo-1-azetidineacetate, from which 5.3 g (28% of theory) of pure product with a melting point of 174°–176° and an $[α]_D^{20} = -115° \pm 1°$ (1% in chloroform) are obtained by crystallisation from ether. The IR and NMR spectra are identical with those for the product obtained according to Example 1.

EXAMPLE 4

20 g (38 mmols) of nocardicin A are dissolved in a suspension of 80 g of $Na_2CO_3$ in 600 ml of dioxan and 300 ml of water. The mixture is warmed to 55° and 26 ml (0.117 mol) of di-tert.-butyl dicarbonate are added dropwise in the course of 6 hours, with stirring. A further 26 ml (0.11 mol) of di-tert.-butyl dicarbonate are added dropwise in the course of a further 20 hours, after which the "absorbance value" of a 1 ml sample diluted to 1 liter is 0.63 (corresponding to 70% conversion). The mixture is cooled to 30°, a further 10 ml (0.045 mol) of di-tert.-butyl dicarbonate are added in the course of 10 minutes and the mixture is again warmed at 55° for 16 hours (according to the UV spectrum the conversion is 79%). This procedure is repeated twice more, after which the "absorbance value" is 0.8 (corresponding to 90% conversion). In order to complete the esterification, 40 g of $Na_2CO_3$ and 8 ml (0.036 mol) of di-tert.-butyl dicarbonate are added all at once to the mixture at room temperature. Two further 8 ml portions are added all at once at intervals of 24 hours, after which the TLC (chloroform:methanol:glacial acetic acid, 25:12:3) indicates complete conversion of free phenol (total consumption of di-tert.-butyl dicarbonate=0.477 mol).

The mixture is cooled to 0°–5° and filtered with suction and the residue is washed thoroughly with 400 ml of 2:1 dioxan:water. At a bath temperature of below 10° (solid carbon dioxide cold trap) the mixture is evaporated in vacuo to half its volume and cooled to 0°–5°. After extracting with twice 500 ml of ice-cooled ethyl acetate, the pH of the aqueous solution is adjusted to 4 with 10 percent citric acid. The mixture is extracted immediately with three 1,500 ml portions of pre-cooled ethyl acetate. The organic phase is washed with two 250 ml portions of pre-cooled sodium chloride solution, dried briefly over magnesium sulfate and evaporated to about 200 ml in vacuo. The product which was precipitated is filtered off with suction, washed with ethyl acetate and absolute ether and dried overnight under a high vacuum, yielding 8.9 g (53% of theory) of pure (3S)-3-tert.-butoxycarbonylamino-(αR)-α-(4-tert.-butoxycarbonyloxyphenyl)-2-oxo-1-azetidineacetic acid with a melting point of 195° (with decomposition); $[α]_D^{20} = -156° \pm 1°$ (in 0.5 M $NaHCO_3$).

EXAMPLE 5

2 g (4.49 mmols) of (3S)-3-tert.-butoxycarbonylamino-(αR)-α-(4-tert.-butoxycarbonyloxyphenyl)-2-oxo-1-azetidineacetic acid are dissolved in 50 ml of dioxan and 1 g (5.2 mmols) of diphenyldiazomethane is added all at once to this solution. After 4 hours no further starting material can be seen in the TLC ($CHCl_3$: MeOH:HOAc, 85:12:3). The red colour is removed by adding two drops of glacial acetic acid and the mixture is evaporated in vacuo at a bath temperature of 25°. The colourless foam is dissolved in 20 ml of absolute ethanol and the product starts to crystallise out. 2.4 g (87% of theory) of pure diphenylmethyl (3S)-3-tert.-butoxycarbonylamino-(αR)-α-(4-tert.-butoxycarbonyloxyphenyl)-2-oxo-1-azetidineacetate with a melting point of 155°–157° are obtained.

EXAMPLE 6

30 ml of dioxan and 2.0 g (0.0038 mol) of nocardicin A are added to a solution of 12 g of sodium carbonate in 30 ml of water. A solution of 3.6 g (0.021 mol) of carbobenzoxy chloride in 25 ml of dioxan is added dropwise in the course of 15 minutes, at 0°–5°. The remainder of the solution is added dropwise in the course of 24 hours at 60° and the mixture is then stirred for a further three days at this temperature. The mixture is cooled to 35° and 4.8 ml of di-tert.-butyl dicarbonate are added dropwise in the course of 24 hours. The mixture is filtered with suction, the material on the filter is washed with 1:1 dioxan:water and the filtrate is evaporated at a temperature below 20°. The residue is suspended in 100 ml of ice-water and the suspension is extracted three times with ethyl acetate. At 0°–5°, the pH of the aqueous phase is adjusted to 4 with 2 N citric acid and this phase is extracted three times with pre-cooled ethyl acetate. The organic phase is washed twice with cold sodium chloride solution, dried over sodium sulfate and evaporated, yielding 2.2 g of a mixture of (3S)-3-benzyloxycarbonylamino-(αR)-α-(4-tert.-butoxycarbonyloxyphenyl)-2-oxo-1-azetidineacetic acid and 4-((3R)-3-benzyloxycarbonylamino-3-carboxypropoxy)-benzonitrile in the form of a rigid foam.

The resulting crude mixture is dissolved in 70 ml of dioxan, 1 g (0.00514 mol) of diphenyldiazomethane is added and the mixture is stirred for three days at room temperature. The reaction mixture is decolorised by adding a little glacial acetic acid and evaporated and the residue is absorbed on 100 g of silica gel and chromatographed with toluene. Elution with 98:2 toluene:ethyl acetate yields 1.8 g of 4-((3R)-3-benzyloxycarbonylamino-3-diphenylmethoxycarbonylpropoxy)-benzonitrile, which is recrystallised from ether and is identical to the product described in Example 7. Further elution with 96:4 toluene:ethyl acetate yields 1.0 g of diphenylmethyl (3S)-3-benzyloxycarbonylamino-(αR)-α-(4-tert.-butoxycarbonyloxyphenyl)-2-oxo-1-azetidineacetate, which is recrystallised from ether. Melting point 153°–154°; $[α]_D^{20} = -99° \pm 1°$. IR absorption spectrum (in $CH_2Cl_2$): characteristic bands at 3,430, 1,767, 1,750 sh, 1,732 sh and 1,510 $cm^{-1}$;

| NMR Spectrum (DMSO-$d_6$) | δ Values (ppm) | Number of H | Assigned to |
|---|---|---|---|
| | 1.50 s | 9 | $-C(CH_3)_3$ |
| | 3.0–3.2 m | 1 | 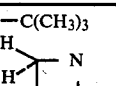 |
| | 3 t (J = 6 + 6Hz) | 1 | |
| | 4.6–4.9 m | 1 | |
| | 5.02 s | 2 | $NHCOOCH_2\phi$ |
| | 5.86 s | 1 | 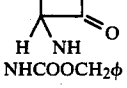 |
| | 6.88 s | 1 | $CH\phi_2$ |
| | 7.0–7.5 m | 19 | Ar—H |
| | 8.02 d | 1 | NH |

EXAMPLE 7

60 ml of dioxan and 4 g (0.0076 mol) of nocardicin A are added to a solution of 24 g of sodium carbonate in 60 ml of water. 10 ml of a solution of 12 g (0.07 mol) of carbobenzoxy chloride in 90 ml of dioxan are added dropwise in the course of 15 minutes, at 0°–5°. The mixture is then warmed to 60° and a further 50 ml of the carbobenzoxy chloride solution are added dropwise in the course of 24 hours. The mixture is then again cooled to room temperature and treated, in the course of 3 hours, with the remainder of the carbobenzoxy chloride solution. The mixture is further stirred overnight and evaporated at room temperature (20°). The residue is dissolved in water and extracted with three times 400 ml of ethyl acetate without washing the organic phase. The ethyl acetate phase, which contains the soluble sodium salts of the products, is evaporated and the semi-crystalline residue (14 g) is suspended in 200 ml of water. At 0°–5°, the pH is adjusted to 3.5 with 2 N hydrochloric acid and the suspension is extracted with three times 200 ml of ethyl acetate. The organic phase is dried over magnesium sulfate and evaporated, yielding 6 g of a crude mixture of (3S)-3-benzyloxycarbonylamino-($\alpha$R)-$\alpha$-(4-benzyloxycarbonyloxyphenyl)-2-oxo-1-azetidineacetic acid and 4-((3R)-3-benzyloxycarbonylamino-3-carboxypropoxy)benzonitrile.

The resulting crude mixture is dissolved in 100 ml of dioxan and 3 g (0.0154 mol) of diphenyldiazomethane are added. The mixture is stirred at room temperature for two days, five drops of glacial acetic acid are added and the mixture is stirred for a further two hours. After evaporating, 8 g of a red resin are obtained and this is chromatographed on 400 g of silica gel. Elution with 98:2 toluene:ethyl acetate yields 0.3 g of 4-((3R)-3-benzyloxycarbonylamino-3-diphenylmethoxycarbonylpropoxy)benzonitrile, which is recrystallised from ether; melting point 125°–126°; $[\alpha]_D^{20} = +1° \pm 1°$; IR absorption spectrum (in $CH_2Cl_2$); characteristic bands at 3,460, 2,240, 1,748 s, 1,737, 1,610 and 1,510 cm$^{-1}$;

| NMR Spectrum (CDCl$_3$) | $\delta$ Values (ppm) | | Number of H | Assigned to |
|---|---|---|---|---|
| | 2.0–2.4 | m | 2 | |
| | 4.10 (J = 6 Hz) | t | 2 | —O—CH$_2$—CH$_2$ |
| | 4.2–4.6 | m | 1 | —CH—CH$_2$ |
| | 5.01 | s | 2 | COOCH$_2\phi$ |
| | 6.8 | s | 1 | CH$\phi_2$ |
| | 6.98 and 7.69 | q | 4 | aromatic A$^2$B$^2$ |
| | 7.29 | s | 15 | remaining aromatic radicals |
| | 7.92 (J = 8 Hz) | d | 1 | NH |

Further elution with 95:5 toluene:ethyl acetate yields 1.7 g of diphenylmethyl (3S)-3-benzyloxycarbonylamino-($\alpha$R)-$\alpha$-(4-benzyloxycarbonyloxyphenyl)-2-oxo-1-azetidineacetate, which is recrystallised from ether. Melting point 95°–100° (with decomposition); $[\alpha]_D^{20} = -90° \pm 1°$; IR absorption spectrum (in $CH_2Cl_2$): characteristic bands at 3,450, 1,770, 1,752 sh, 1,735 sh and 1,510 cm$^{-1}$.

| NMR Spectrum (CDCl$_3$) | $\delta$ Values (ppm) | Number of H | Assigned to |
|---|---|---|---|
| | 3.10 q (J = 3 + 6Hz) | 1 | H, H—, H, NH— / N, =O (ring structure) |
| | 3.87 t (J = 6 + 6 Hz) | 1 | |
| | 4.65–4.93 m | 1 | |
| | 5.09 s | 2 | O—COOCH$_2\phi$ |
| | 5.31 s | 2 | NHCOOCH$_2\phi$ |
| | 5.45 d (J = 8Hz) | 1 | —NH— |
| | 6.96 s | 1 | —CH$\phi_2$ |
| | 7.0–7.5 m | 24 | aromatic H |

EXAMPLE 8

The pH of a suspension of 160 g (0.31 mol) of nocardicin A monohydrate (free acid) in 1.6 liters of water is adjusted to 10.2 by adding saturated sodium hydroxide solution. 1 liter of dioxan and 200 ml (0.99 mol) of di-tert.-butyl dicarbonate are added to the clear colourless solution and the mixture is stirred at 55° for 3 hours. During the entire reaction time, the pH value is kept between 9.8 and 10.2 by adding concentrated sodium hydroxide solution by means of a titrator. An additional 150 ml (0.74 mol) of di-tert.-butyl dicarbonate are then added dropwise in the course of a further 4 hours, after which the absorption at 250 nm reaches a maximum. Prior to working up, the mixture is cooled to 30° and a further 250 ml (1.24 mols) of di-tert.-butyl dicarbonate are added dropwise in the course of 24 hours. The mixture is filtered with suction, the residue is washed with 500 ml of dioxan and the filtrate is evaporated to 2.5–3 liters in vacuo at 20°. The mixture is extracted with 1 liter of ethyl acetate, cooled to 5° and acidified to pH 4.2 with concentrated hydrochloric acid. The product crystallises out after a few minutes. The mixture is filtered with suction and the residue is washed with 500 ml of water and 1,500 ml of ethyl acetate in portions, yielding 108.1 g (80% of theory) of (3S)-3-tert.-butoxycarbonylamino-($\alpha$R)-$\alpha$-(4-tert.-butoxycarbonyloxyphenyl)-2-oxo-1-azetidineacetic acid with a melting point of 173° (decomposition).

48 g (51% of theory) of 4-((3R)-3-tert.-butoxycarbonylamino-3-carboxypropoxy)-benzonitrile with a melting point of 132°–146° are obtained from the ethyl acetate wash solutions after evaporating to about 200 ml.

EXAMPLE 9

A mixture of 1.5 g of diphenylmethyl (3S)-3-(tert.-butoxycarbonylamino)-($\alpha$R)-$\alpha$-(4-tert.-butoxycarbonyloxyphenyl)-2-oxo-1-azetidineacetate in 45 ml of acetonitrile and 1.5 g of p-toluenesulfonic acid monohydrate is stirred at room temperature for 75 minutes, during which time the toluene sulfonate of diphenylmethyl (3S)-3-amino-($\alpha$R)-$\alpha$-(4-tert.-butoxycarbonyloxyphenyl)-2-oxo-1-azetidineacetate partially crystallises out. The mixture is diluted with ethyl acetate, rendered basic with 1 N aqueous NaHCO$_3$ solution, washed with saturated aqueous NaCl solution until neutral, dried over Na$_2$SO$_4$ and evaporated in vacuo. The resulting crude product is chromatographed on 100 g of silica gel. 111 mg of the unconverted starting ester are eluted with a 4:1 mixture of toluene and ethyl acetate. Subsequent 1:1 toluene/ethyl acetate and ethyl acetate functions yield 950 mg of diphenylmethyl (3S)-3-amino- (αR)-α-(4-tert.-butoxycarbonyloxyphenyl)-2-oxo-1-azetidineacetate; melting point 120°–122° after crystallisation from ether. IR spectrum (CH$_2$Cl$_2$): characteristic bands at 3,400–2,500 (broad), 1,760 (shoulder) and 1,750 cm$^{-1}$; UV spectrum (in ethanol): $\lambda_{max}$ at 252 nm ($\epsilon=620$), 257 nm ($\epsilon=720$) and shoulders at 263 and 267 nm, and also a strong end absorption; NMR spectrum (in CDCl$_3$; ppm): 1.57, s, C(CH$_3$)$_3$; 3.05, dd, $J_{2,2}=5$, $J_{2,3}=2.5$, CH-2; 3.81, t, $J_{2,2}=J_{2,3}=5$, CH-2; 4.32, bm, CH-3; 5.64, s, CHCOO; 6.87, s, CHPh$_2$; 7.00–7.30, diverse m, 14 aromatic H.

EXAMPLE 10

500 mg of (3S)-3-tert.-butoxycarbonylamino-(αR)-α-(4-tert.-butoxycarbonyloxyphenyl)-2-oxo-1-azetidineacetic acid are stirred in 10 ml of trifluoroacetic acid for 10 minutes at 0°. The mixture is then diluted with ethyl acetate and washed three times with water. The pH of the combined aqueous extracts is then adjusted to 4.5 by adding Amberlite IR 45 (OH form). The ion exchanger is filtered off and washed with water and the resulting filtrate is substantially evaporated in vacuo at a bath temperature of 50°. On adding ethanol to the aqueous solution, which has been concentrated to about 5 ml, crystallisation of (3S)-3-amino-(αR)-α-(4-hydroxyphenyl)-2-oxo-1-azetidineacetic acid takes place and this product is then filtered off, washed with ether and dried under a high vacuum. Yield: 80 mg. Melting point: decomposition above 200°. IR spectrum (in Nujol): characteristic bands at 3,175, 2,688, 2,597, 2,500, 2,325, 1,776, 1,754, 1,639, 1,589, 1,519, 1,499 and 1,464 cm$^{-1}$; NMR spectrum (D$_2$O + 1 equivalent of NaHCO$_3$): 3.30, dd, $J_{2,2}=5$, $J_{2,3}=2.5$ CH-2; 4.10, t, $J_{2,2}=J_{2,3}=5$ CH-2; 4.64, dd, $J_{2,3}=5$ and 2.5, CH-3; 5.57, s, CHCOO; 7.21+7.53, 2d, J=8.4 aromatic H.

EXAMPLE 11

A mixture of 700 mg of diphenylmethyl (3S)3-(tert.-butoxycarbonylamino)-(αR)-α-(4-tert.-butoxycarbonylphenyl)-2-oxo-1-azetidineacetate and 1.5 ml of anisole in 20 ml of CF$_3$COOH is stirred at 0° for 10 minutes. The mixture is evaporated to dryness in vacuo (bath temperature 30°) and the residue is taken up three times successively in chloroform and toluene, the solution being evaporated to dryness in vacuo each time. The residue is then dried in vacuo for 1 hour, digested in ether, filtered off from the ether and again dried in vacuo for 1 hour. It is then dissolved in 5 ml of methanol, 50 ml of water are added and the mixture is extracted with ethyl acetate, the extracts being additionally washed three times with water. The pH of the combined aqueous fractions is adjusted to 4.5 by adding Amberlite IR 45 (OH form) and the ion exchanger is then removed by filtration and washed thoroughly with water. The filtrate is then concentrated to 5 ml in vacuo (bath temperature 50°) and the product is crystallised by adding ethanol. The crystalline (3S)-3-amino-(αR)-α-(4-hydroxyphenyl)-2-oxo-1-azetidineacetic acid is filtered off, washed with ether and dried under a high vacuum. Yield: 137 mg. Melting point: decomposition above 200°.

EXAMPLE 12

700 mg of diphenylmethyl (3S)-3-amino-(αR)-α-(4-tert.-butoxycarbonyloxyphenyl)-2-oxo-1-azetidineacetate are reacted as in Example 11 and the product is worked up. 93 mg of (3S)-3-amino-(αR)-α-(4-hydroxyphenyl)-2-oxo-1-azetidineacetic acid result. Melting point: decomposition above 200°.

EXAMPLE 13

700 mg of diphenylmethyl (3S)-3-tert.-butoxycarbonylamino-(αR)-α-(4-hydroxyphenyl)-2-oxo-1-azetidineacetate are reacted as in Example 11 and the product is worked up. 40 mg of (3S)-3-amino-(αR)-α-(4-hydroxyphenyl)-2-oxo-1-azetidineacetic acid result; melting point: decomposition above 200°.

EXAMPLE 14

5.95 g (0.03 mol) of p-toluenesulfonic acid monohydrate are added to a solution of 5.95 g (0.0098 mol) of diphenylmethyl (3S)-3-(tert.-butoxycarbonylamino)-(αR)-α-(4-tert.-butoxycarbonyloxyphenyl)-2-oxo-1-azetidineacetate in 180 ml of absolute acetonitrile, at room temperature with stirring.

The yellow solution thus obtained is stirred for a further 75 minutes at room temperature and after only 20 minutes some of the p-toluenesulfonate crystallises out. The mixture is then cooled to −10°, 400 ml of absolute ether are added and crystallisation is brought to completion by stirring for 1 hour at −10°. The product thus obtained is filtered off with suction, washed with absolute ether and dried at 50° under a high vacuum. After recrystallising once from isopropanol, 2.9 g (43.5% of theory) of the pure p-toluenesulfonate of diphenylmethyl (3S)-3-amino-(αR)-α-(4-tert.-butoxycarbonyloxyphenyl)-2-oxo-1-azetidineacetate are obtained in the form of white crystals with a melting point of 150°–151° (decomposition).

EXAMPLE 15

20 g of (3S)-3-tert.-butoxycarbonylamino-(αR)-α-(4-tert.-butoxycarbonyloxyphenyl)-2-oxo-1-azetidineacetic acid are introduced into 100 ml of trifluoroacetic acid at 0°–5°. After the evolution of CO$_2$ has ceased (~8 minutes), the reaction mixture is substantially freed from excess trifluoroacetic acid under a high vacuum. The residue is digested with 100 ml of dry ether, filtered off, washed with ether and dried in vacuo at room temperature. The resulting trifluoroacetate of (3S)-3-amino-(αR)-α-(4-hydroxyphenyl)-2-oxo-1-azetidineacetic acid is dissolved in 80 ml of methanol and the pH of the solution is adjusted to 4.3 by adding 30% methanolic triethylamine solution. The (3S)-3-amino-(αR)-α-(4-hydroxyphenyl)-2-oxo-1-azetidineacetic acid which crystallises out is filtered off and washed with methanol; melting point: 196°–200°; yield: 9.3 g (~86% of theory).

EXAMPLE 16

A suspension of 9 g (21 mmols) of (3S)-3-tert.-butoxycarbonylamino-(αR)-α-(4-tert.-butoxycarbonyloxyphenyl)-2-oxo-1-azetidineacetic acid and 2.23 g (21 mmols) of Na$_2$CO$_3$ in 60 ml of H$_2$O is warmed at 60° for 2 hours (pH 9). After 2 hours it is filtered and the pH of the clear colourless solution is adjusted to 2 with 2 N HCl. The precipitate is filtered off, washed with water and ethyl acetate and recrystallised from ethyl acetate and methanol. 5.8 g (~82%) of (3S)-3-(tert.-butoxycarbonylamino)-(αR)-α-(4-hydroxyphenyl)-2-oxo-1-azetidineacetic acid are obtained. Melting point: decomposition above 201°.

EXAMPLE 17

4.55 g of (3S)-3-(tert.-butoxycarbonylamino)-(αR)-α-(4-hydroxyphenyl)-2-oxo-1-azetidineacetic acid are dissolved in 100 ml of methanol, and 5 g of diphenyldiazomethane in 30 ml of chloroform are added at room temperature. The mixture is stirred for 3 hours at room temperature, the excess diphenyldiazomethane is decomposed with glacial acetic acid and the product is taken up in ethyl acetate and the ethyl acetate solution is washed successively with saturated aqueous solutions of NaHCO₃ and NaCl (to the neutral point). It is then dried over Na₂SO₄ and evaporated in vacuo and the resulting crude product is chromatographed on 250 g of silica gel. The 1:1 toluene/ethyl acetate eluates which contain a single compound are combined and evaporated and the residue is then recrystallised from acetone/petroleum ether. This yields 6.4 g of diphenylmethyl (3S)-3-tert.-butoxycarbonylamino-(αR)-α-(4-hydroxyphenyl)-2-oxo-1-azetidine-acetate with a melting point of 176°–178° (decomposition). $[\alpha]_D^{20} = -111°$ (c = 0.92 in CHCl₃). IR spectrum (CH₂Cl₂): characteristic bands at 3,580, 3,420, 1,760, 1,742, 1,720, 1,618, 1,600 and 1,518 cm⁻¹.

EXAMPLE 18

1.0 ml of ethyldiisopropylamine is added to a solution of 1.8 g (5.5 mmols) of 4-((3R)-3-tert.-butoxycarbonylamino-3-carboxypropoxy)-benzonitrile in 20 ml of methanol and the mixture is stirred for 15 minutes at room temperature. After adding 1.2 g of dianilinoethane dihydrochloride and 1.5 g of Raney nickel, the mixture is hydrogenated until the reaction has ceased. The catalyst is filtered off, the filtrate is evaporated and the resinous residue is partitioned between 50 ml of ice-cooled 2 N hydrochloric acid and 50 ml of chloroform. The organic phase is washed with ice-cooled 2 N hydrochloric acid and water, dried over magnesium sulfate and evaporated, yielding 0.9 g of a solid residue. The latter is recrystallised from isopropanol/ether and yields 4-((3R)-3-tert.-butoxycarbonylamino-3-carboxypropoxy)benzaldehyde with a melting point of 147°–149° (with decomposition); $[\alpha]_D^{20} = -7° \pm 1°$, (0.523% in 0.5 N NaHCO₃); IR spectrum (in dioxan): characteristic absorption bands at 3,210, 1,740, 1,715, 1,700, 1,605 and 1,580 cm⁻¹.

EXAMPLE 19

1.2 g (6.67 mmols) of diphenyldiazomethane are added to a solution of 2.0 g (6.19 mmols) of 4-((3R)-3-tert.-butoxycarbonyl-amino-3-carboxypropoxy)-benzaldehyde in 50 ml of dioxan and the mixture is stirred for 24 hours at room temperature. The mixture is evaporated and the resinous residue is stirred repeatedly with a little cyclohexane, whereupon the residue starts to solidify. By filtering off with suction, a crude product is obtained and this is recrystallised from ether, yielding 4-((3R)-3-tert.-butoxycarbonylamino-3-benzhydryloxycarbonylpropoxy)-benzaldehyde with a melting point of 116°–119°; $[\alpha]_D^{20} = -5° \pm 1°$ (0.588% in CHCl₃); IR spectrum (in CH₂Cl₂): characteristic absorption bands at 3,420, 2,730, 1,740, 1,712, 1,695, 1,605 and 1,580 cm⁻¹.

EXAMPLE 20

In a dry apparatus, 0.476 g (0.97 mmol) of 4-((3R)-3-tert.-butoxycarbonylamino-3-benzhydryloxycarbonylpropoxy)-benzaldehyde is dissolved in a mixture of 25 ml of ether and 3 ml of tetrahydrofuran. Under nitrogen as a blanketing gas, 3.3 mmols of methylmagnesium iodide, freshly prepared from 0.081 g of magnesium turnings and 0.2 ml of methyl iodide in 10 ml of ether, are added dropwise in the course of 15 minutes, at 0°–5°, and the temperature is then raised to room temperature. The mixture is poured into 50 ml of 10% ammonium chloride solution which contains a little ice, and the aqueous phase is separated off. The organic phase is washed with water and dried over magnesium sulfate. After evaporating, a colourless mixture of the two diastereomeric 4-((3R)-tert.-butoxycarbonylamino-3-benzhydryloxycarbonylpropoxy)-phenylmethylcarbinols is obtained and this can be oxidised with manganese dioxide without further purification.

EXAMPLE 21

0.70 g (1.38 mmols) of 4-((3R)-3-tert.-butoxycarbonylamino-3-benzhydrylcarbonylpropoxy)-phenylmethylcarbinol (mixture of diastereomers) is dissolved in 100 ml of methylene chloride, 3 g of manganese dioxide are added to the solution and the mixture is stirred overnight at room temperature. The mixture is filtered and the filtrate is evaporated, whereupon a yellow solidified foam is obtained. On the addition of a little ether, 4-((3R)-tert.-butoxycarbonylamino-3-benzhydryloxycarbonylpropoxy)-phenyl methyl ketone with a melting point of 102°–104° is obtained; $[\alpha]_D^{20} = 0° \pm 1°$ (0.5% in CHCl₃); IR spectrum (in CH₂Cl₂): absorption bands at 3,240, 1,740, 1,710, 1,675, 1,600 and 1,575 cm⁻¹.

EXAMPLE 22

0.204 g (1.84 mmols) of selenium dioxide is added to a solution of 0.310 g (0.615 mmol) of 4-((3R)-3-tert.-butoxycarbonylamino-3-benzhydryloxycarbonylpropoxy)phenyl methyl ketone in 3 ml of pyridine. The mixture is stirred for 16 hours at 80°, cooled to room temperature and filtered and the clear filtrate is evaporated. The residue is suspended in 10 ml of water and the pH is adjusted to 2.5 with ice-cooling. The mixture is then extracted with twice 50 ml of ethyl acetate. The organic phase is washed with water, dried over magnesium sulfate and evaporated. Crude 4-((3R)-3-tert.-butoxycarbonylamino-3-benzhydryloxycarbonylpropoxy)-phenylglyoxylic acid is obtained.

What is claimed is:

1. A method for the preparation of a 3-amino-2-oxoazetidine compound of the formula

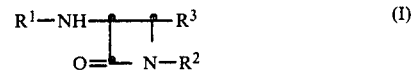

(I)

in which R¹ denotes hydrogen or a group of the formula R$_a$¹—O—C(=O)—, in which R$_a$¹ denotes lower alkyl, oxo-lower alkyl, halogeno-lower alkyl, cyano-lower alkyl, cycloalkyl, phenyl, phenyl substituted by one to five halogen, one or two lower alkoxy, or one or two nitro, benzyl or diphenylmethyl which can be monosubstituted in the aromatic radical by halogen, lower alkoxy or nitro, R² denotes hydrogen, 1-carboxy-lower alkyl, 1-carboxy-1-phenylmethyl, in which the phenyl ring is unsubstituted or monosubstituted to trisubstituted by lower alkyl, halogen, nitro, amino, hydroxy, lower alkoxy, acetoxy, and/or carbamoyloxy, 1-carboxy-1-heterocyclylmethyl, in which heterocyclyl is thienyl, furyl, thiadiazolyl monosubstituted by lower alkyl, or benzthiazolyl, 1-amino-lower alkyl, in which lower alkyl contains one to four C atoms, 1-hydroxy-lower alkyl, in which lower alky contains one to four C atoms and hydroxyl can be replaced by lower alkoxy, acetoxy or carbamoyloxy, 1-carboxy-lower alkenyl, in which lower alkenyl contains two or four C atoms and can be substituted by phenyl or phenylthio, in which groups $R^2$ the carboxyl group can be replaced by lower alkoxycarbonyl, pivaloyloxymethoxycarbonyl, halogeno-lower alkoxycarbonyl, benzyloxycarbonyl, 4-methoxybenzyloxycarbonyl, 4-nitrobenzyloxycarbonyl, diphenylmethoxycarbonyl, 4,4′-dimethoxydiphenyl-methoxycarbonyl, cycloalkyloxycarbonyl, phenoxycarbonyl, 2- or 4- nitrophenoxycarbonyl, 4-methoxyphenyloxycarbonyl, halogenophenoxycarbonyl, aminocarbonyl, anilinocarbonyl, hydrazinocarbonyl or azidocarbonyl, and in which groups $R^2$ amino can be substituted by one or two lower alkyl, one acetyl, a group $R_1{}^a$—O—C(=O)—, 2-halogenoacetyl, benzyl, 4-methoxybenzyl, 2- or 4-nitrobenzyl, diphenylmethyl or phthaloyl, and in which groups $R^2$ hydroxyl can be substituted by lower alkyl, acetyl, carbamoyl, a group $R_1{}^a$—O—C(=O)—, 2-halogenoacetyl, benzyl, 4-methoxybenzyl, 2- or 4-nitrobenzyl or diphenylmethyl, and $R^3$ denotes hydrogen, hydroxymethyl, wherein hydroxy can be protected by a group $R_1{}^a$—O—C(=O)—, 2-halogenoacetyl, benzyl, 4-methoxybenzyl, 2- or 4-nitrobenzyl or diphenylmethyl, phenyl or 2-phenylvinyl, and a conventional salt of such compound containing a salt-forming group, and/or of a nitrile of the formula R°—CN, in which R° denotes ω-carboxyl-ω-amino-propoxyphenyl, wherein the ω-amino group can be protected by a group of the formula $R_1{}^a$—O—C(=O)— and carboxyl can be protected in esterified form by lower alkyl, lower alkanoyloxymethyl, 2,2,2-trichloroethyl, benzyl, 4-methoxybenzyl, 2- or 4-nitrophenyl or diphenylmethyl, and a conventional salt of such compound containing a salt-forming group, which comprises treating a 3-(2-hydroxyimino-acetylamino)-2-oxoazetidine compound of the formula

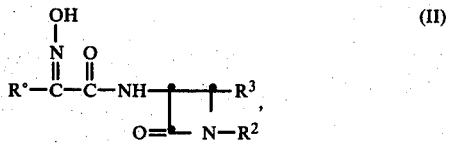

in which $R_2$ and $R_3$ are as defined above and R° denotes phenyl, hydroxyphenyl, lower alkoxyphenyl, lower alkenyloxyphenyl, aralkyloxyphenyl, lower alkoxycarbonyl-lower alkoxyphenyl, carboxy-lower alkoxyphenyl, ω-carboxy-ω-hydroxy-lower alkoxyphenyl, ω-carboxy or ω-lower alkoxycarbonyl-lower alkoxyphenyl, ω-amino-lower alkoxyphenyl, ω-carboxy-ω-amino-lower alkoxyphenyl, furyl, thienyl, thiazolyl, which heterocyclic radicals can be monosubstituted by hydroxy, halogen or amino, in which groups R° hydroxy and amino groups can be protected by a group $R_1{}^a$—O—C(=O)—, and carboxy can be protected in esterified form by lower alkyl, lower alkanoyloxymethyl, 2,2,2-trichloroethyl, benzyl, 4-methoxybenzyl, 2- or 4-nitrobenzyl or diphenylmethyl, or a conventional salt of such a compound containing a salt forming group, in an aqueous medium in the presence of a base, with a compound which is an anhydride or a mixed anhydride with a hydrogen halide of a carbonic acid half-ester of the formula $R_1{}^a$—O—C(=O)—OH, in which $R_1{}^a$ is as defined above, isolating a compound of the formula I, wherein $R^1$ is a group of the formula $R_a{}^1$—O—C(=O)—, and/or isolating a nitrile R°—CN, in which R° denotes ω-carboxyl-ω-aminopropoxyphenyl, wherein the ω-amino group can be protected by a group of the formula $R_1{}^a$—O—C(=O)— and carboxyl can be protected in esterified form by lower alkyl, lower alkanoyloxymethyl, 2,2,2-trichloroethyl, benzyl, 4-methoxybenzyl, 2- or 4-nitrophenyl, or diphenylmethyl and, if desired in a resulting compound liberating the protected hydroxy, amino and/or carboxy groups present by detaching the protective groups, or protecting in a conventional form free hydroxy, amino and/or carboxy groups present, and, when required, converting a resulting compound containing a salt-forming group to a conventional salt or converting a resulting salt to a free compound.

2. A procedure according to claim 1, wherein a nitrile of the formula R°—CN is prepared in which R° is 4-(3-carboxy-3-aminopropoxy)-phenyl, in which carboxyl can be in an esterified form, and amino can be acylated by a group $R_a{}^1$—O—C(=O)— as defined in claim 1, and in which the phenyl group can be substituted by halogen.

3. A procedure according to claim 1, wherein a compound of the formula I is prepared in which $R^1$ is hydrogen or a group of the formula $R_a{}^1$—O—C(=O)—, in which $R_a{}^1$ is tert.-butoxycarbonyl or benzyloxycarbonyl.

4. A procedure according to claim 1, wherein nocardicin A is reacted with di-tert.-butyl dicarbonate and/or with benzyloxycarbonyl chloride and a resulting compound of the formula I, or a salt thereof, and/or a resulting nitrile of the formula R°—CN, or a salt thereof, is isolated.

5. A procedure according to claim 1, wherein a compound of the formula I is prepared in which $R^2$ is α-carboxy-4-hydroxybenzyl, α-carboxy-4-benzyloxycarbonyloxybenzyl, α-carboxy-4-tert.-butoxycarbonyloxybenzyl, α-diphenylmethoxycarbonyl-4-hydroxybenzyl, α-diphenylmethoxycarbonyl-4-tert.-butoxybenzyl or α-diphenylmethoxy-4-benzyloxycarbonyloxybenzyl.

6. A procedure according to claim 1, wherein nocardicin A is employed as the starting material of the formula II.

7. A procedure according to claim 1, wherein a compound of the formula I is prepared in which $R^3$ is hydrogen.

8. A procedure according to claim 1, wherein (3S)-3-tert.-butoxycarbonylamino-(αR)-α-(4-hydroxyphenyl)-2-oxo-1-azetidineacetic acid is prepared.

9. A procedure according to claim 1, wherein diphenylmethyl (3S)-3-tert.-butoxycarbonylamino-(αR)-α-(4-hydroxyphenyl)-2-oxo-1-azetidineacetate is prepared.

10. A procedure according to claim 1, wherein (3S)-3-tert.-butoxycarbonylamino-(αR)-α-(4-tert.-butoxycarbonyloxyphenyl)-2-oxo-1-azetidineacetate acid is prepared.

11. A procedure according to claim 1, wherein diphenylmethyl (3S)-3-tert.-butoxycarbonylamino-(αR)-α-(4-tert.-butoxycarbonyloxyphenyl)-2-oxo-1-azetidineacetic is prepared.

12. A procedure according to claim 1, wherein diphenylmethyl (3S)-3-amino-(αR)-α-(4-tert.-butoxycarbonyloxyphenyl)-2-oxo-1-azetidineacetate or a salt thereof is prepared.

13. A procedure according to claim 1, wherein the reactive derivative of a carbonic acid half-ester of the formula $R_a{}^1$—O—C(=O)—OH is added at a temperature between room temperature and about 100° and the fragmentation is allowed to take place between 40° and 80°.

14. A procedure according to claim 1, wherein the reactive derivative of a carbonic acid half-ester of the formula $R_a{}^1$—O—C(=O)—OH which is used is an anhydride, a mixed anhydride or a reactive ester thereof.

* * * * *